United States Patent [19]

Sugiyama et al.

[11] Patent Number: 4,817,619
[45] Date of Patent: Apr. 4, 1989

[54] ULTRASONIC DIAGNOSIS APPARATUS

[75] Inventors: Takashi Sugiyama; Satoshi Tamano, both of Kashiwa; Yukio Ito, Tokyo, all of Japan

[73] Assignee: Hitachi Medical Corp., Tokyo, Japan

[21] Appl. No.: 839,508

[22] Filed: Mar. 14, 1986

[30] Foreign Application Priority Data

Jun. 24, 1985 [JP] Japan .................................. 60-136012

[51] Int. Cl.⁴ ............................................. A61B 10/00
[52] U.S. Cl. ............................... 128/661.09; 73/861.25
[58] Field of Search ................................ 128/660–663; 73/861.25

[56] References Cited

U.S. PATENT DOCUMENTS

| | | | |
|---|---|---|---|
| 4,257,278 | 3/1981 | Papodofrangakis et al. | 128/663 |
| 4,413,630 | 11/1983 | Anderson et al. | 128/661 |
| 4,573,477 | 3/1986 | Namekowa et al. | 128/663 |
| 4,612,937 | 9/1986 | Miller | 128/663 |
| 4,622,978 | 11/1986 | Matsuo et al. | 128/663 |
| 4,641,668 | 2/1987 | Namekowa et al. | 128/663 |

OTHER PUBLICATIONS

Ostro, P. T. et al., "Digital UTS Imaging with Microprocessor Manipulation", J MET, vol. 2 #5, Sep. 1978, pp. 234–238.

Primary Examiner—Francis J. Jaworski
Attorney, Agent, or Firm—Antonelli, Terry & Wands

[57] ABSTRACT

An ultrasonic diagnosis apparatus obtains an ultrasonic wave image of B mode by transmitting an ultrasonic pulse beam toward an internal moving part of a living body at a constant recurrence frequency and receiving the reflected wave therefrom. A speed distribution operator detects a frequency shift of the reflected wave Doppler-shifted by the internal moving part, thereby computing the distribution of the moving speed of the internal moving part. The speed distribution image of the internal moving part is displayed on the basis of the output of the speed operator. The apparatus includes distribution a circuit section for variably designating the region of scanning with the ultrasonic pulse beam for the measurement of the Doppler blood flow image so that the region can be selected as desired.

13 Claims, 8 Drawing Sheets

ULTRASONIC DIAGNOSIS APPARATUS

BACKGROUND OF THE INVENTION

This invention relates to an ultrasonic diagnosis apparatus adapted to display a Doppler blood flow image on a display unit.

An ultrasonic diagnosis apparatus measuring the speed of blood flow in a living body is required to transmit ultrasonic pulses a plurality of times into the living body in the same direction, so as to measure a Doppler frequency shift of the reflected wave due to the blood flow and to display the result of measurement as a Doppler blood flow image. However, in a prior art ultrasonic diagnosis apparatus in which both the angle of scanning with an ultrasonic pulse beam and the region of Doppler blood flow image display on a display unit are fixed, the frame rate of a Doppler blood flow image is only about 1/n (n: a positive integer less than ten) of that of a B-mode image when a scanning area for the Doppler blood flow image and that for the B-mode image are the same, and the rate of appearance of flickering is higher in the former image than the latter image. Further, due to the fact that the direction of transmission of the ultrasonic pulse beam transmitted from an ultrasonic probe for the measurement of the Doppler blood flow image is fixed relative to the ultrasonic probe in the prior art ultrasonic diagnosis apparatus, there has been a problem that those having a considerable skill in this kind of measurement can only determine the position and direction of the ultrasonic probe relative to a living body or an object to be diagnosed.

SUMMARY OF THE INVENTION

It is a primary object of the present invention to provide an ultrasonic diagnosis apparatus adapted to display a two-dimensional speed distribution image of an internal moving part of a living body, in which the image completion time restricted by the velocity of sound can be shortened so as to increase the frame rate of a Doppler blood flow image.

Another object of the present invention is to provide an ultrasonic diagnosis apparatus which is improved in its operability.

The ultrasonic diagnosis apparatus according to the present invention comprises means which can freely or variably designate the angle and/or the depth of scanning with an ultrasonic pulse beam for the measurement of a Doppler blood flow image, so as to shorten the completion time of the Doppler blood flow image, that is, to improve the frame rate of the Doppler blood flow image.

The ultrasonic diagnosis apparatus according to the present invention may also comprise means which can freely or variably designate the direction of scanning for the measurement of the Doppler blood flow image. Therefore, the region of image display on a display unit can be shifted to the right or left with respect to a centerline as desired, while maintaining an ultrasonic probe in its fixed position, so that the operability of the apparatus can be improved.

Two or more means selected from among the scanning angle designating means, scanning depth designating means and scanning direction designating means can be combined as required.

DESCRIPTION OF THE PREFERRED EMBODIMENTS

The present invention will now be described in detail with reference to the drawings.

Figure 1:
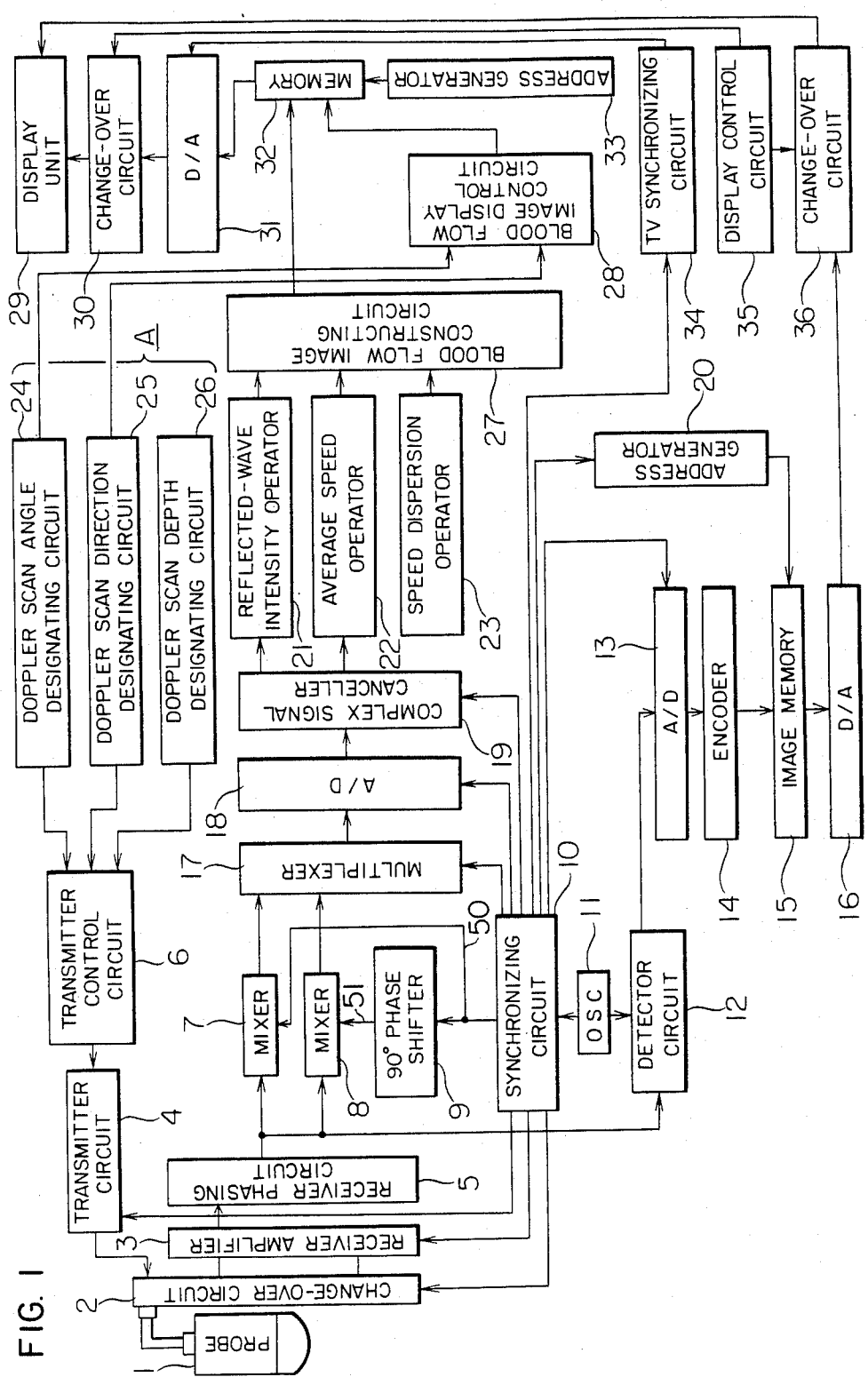
FIG. 1 is a block diagram showing the general structure of a preferred embodiment of the ultrasonic diagnosis apparatus according to the present invention.

FIG. 1 is a block diagram showing the general structure of a preferred embodiment of the ultrasonic diagnosis apparatus according to the present invention.

Referring to FIG. 1, a crystal oscillator 11 generates and applies a stable high-frequency signal to a synchronizing circuit 10 which generates various output signals having a desired frequency. These output signals include a signal for causing repeated transmission of an ultrasonic pulse beam, a reference signal used for converting echoes into a complex signal, a TV synchronizing signal for displaying the result of ultrasonic diagnosis, and a clock signal for attaining synchronous operation of various parts of the ultrasonic diagnosis apparatus.

The signal for causing repeated ultrasonic pulse beam transmission is applied through a transmitter circuit 4 and a change-over circuit 2 to an ultrasonic probe 1, and vibrators provided in the ultrasonic probe 1 are excited to transmit an ultrasonic pulse beam toward and into an object or an internal moving part of a living body to be diagnosed. This internal moving part is, for example, blood flow. The ultrasonic diagnosis apparatus according to the present invention comprises a section A for designating the region of scanning for the measurement of a Doppler blood flow image. This section A includes a Doppler scan angle designating circuit 24 designating the angle of scanning for the measurement of the Doppler blood flow image, a Doppler scan direction designating circuit 25 designating the direction of scanning for the measurement of the Doppler blood flow image, and a Doppler scan depth designating circuit 26 designating the depth of scanning for the measurement of the Doppler blood flow image. A transmitter control circuit 6 controls the transmitter circuit 4 so that an ultrasonic pulse beam meeting the scanning angle, direction and depth designated by the respective designating circuits 24, 25 and 26 can be transmitted toward and into the living body to be diagnosed.

Pulses of the transmitted ultrasonic beam reflected from the internal moving part of the living body are received by the ultrasonic probe 1. The received echo signal is high-frequency amplified by a receiver amplifier 3, and the high-frequency output signal of the receiver amplifier 3 is phased by a receiver phasing circuit 5. The output signal of the phasing circuit 5 is demodulated by a detector circuit 12, and the output signal of the detector circuit 12 is converted into a digital signal by an analog/digital (A/D) converter 13. The output signal of the A/D converter 13 is encoded by an encoder 14 into a signal having a level corresponding to that of the demodulated signal and is then stored in an image memory 15. An address generator 20 generates and applies a write/read address signal to the image memory 15. Image information read out from the image memory 15 is applied to a display unit 29 as a display signal of B mode or M mode in a usual manner.

The echo signal, received by the ultrasonic probe 1 and then amplified and phased, is applied also to a first mixer 7 to be demodulated. For this purpose, the aforementioned reference signal 50 having a frequency corresponding to the vibration frequency of the ultrasonic probe 1 is applied to the mixer 7 from the synchronizing circuit 10 for the conversion of the echo signal into a complex signal. On the other hand, the phase of the reference signal 50 is shifted by 90° by a phase shifter 9, and the 90°-phase shifted reference signal 51 is applied, together with the amplified and phased echo signal, to a second mixer 8 to be demodulated, so as to indicate the direction of blood flow in the living body to be diagnosed. The demodulated output signals of the mixers 7 and 8 are converted into a time serial signal by a multiplexer 17. This time serial signal is then converted into a digital signal by an A/D converter 18 for the purpose of later digital processing.

A complex signal canceller 19 is provided so that echo signal components Doppler-shifted by blood flow can only be extracted from the Doppler signal components carrying the information of the internal moving part of the living body and so that echo signal components reflected from a stationary part and a part such as the wall of the heart whose speed is lower than that of blood flow in the living body can be removed.

As means for computing the speed of the internal moving part of the living body on the basis of the complex signal which is extracted by the complex signal canceller 19 and which has been Doppler-shifted by the blood flow, there are provided a reflected-wave intensity operator 21 computing the intensity of the reflected wave from the internal moving part of the living body, an average speed operator 22 computing the average Doppler shift frequency, that is, the relative speed of the blood flow dependent upon the direction of the transmitted ultrasonic beam and the direction of blood flow, and a speed dispersion operator 23 computing the dispersion of the relative speed described above. In order to display the image of blood flow on the basis of the results of computation by these operators 21 to 23 on the display unit 29, a blood flow image constructing circuit 27 connected to the operators 21 to 23 produces an output signal indicative of the results of computation by the operators 21 to 23.

The structure and operation of the parts, except the section A designating the region of scanning for the measurement of the Doppler blood flow image, are described in detail in co-pending U.S. Ser. No. 804,608 filed on Dec. 4, 1985 and assigned to the same assignee as this applicant, and reference is to be made to that application.

The manner of variably setting the Doppler blood flow image scanning region, that is, how to variably set the angle and direction of scanning and the depth of diagnosis, according to the present invention will now be described in detail. The details of the transmitter control circuit 6, Doppler scan angle designating circuit 24, Doppler scan direction designating circuit 25 and Doppler scan depth designating circuit 26 will be described with reference to FIGS. 2 to 14.

Figure 2:
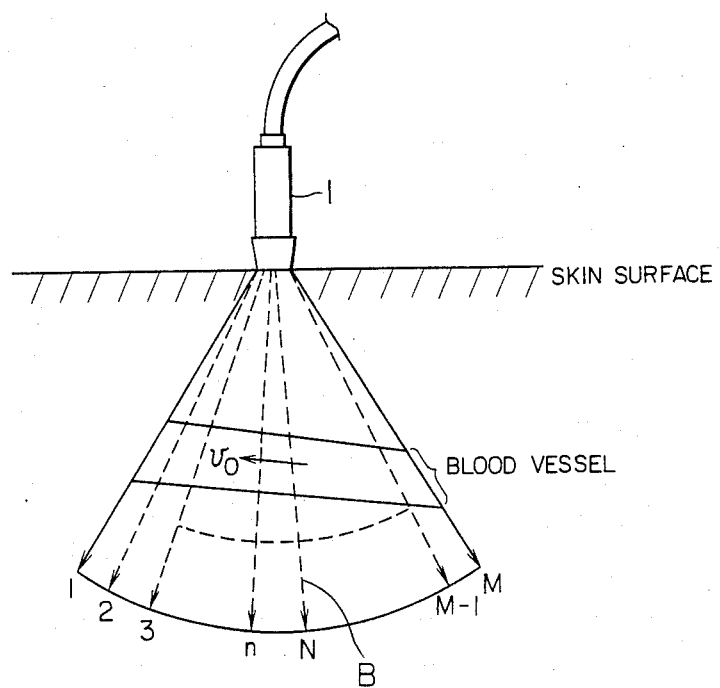
FIG. 2 illustrates schematically the principle of measurement of the speed of an internal moving part of a living body.
Figure 3:
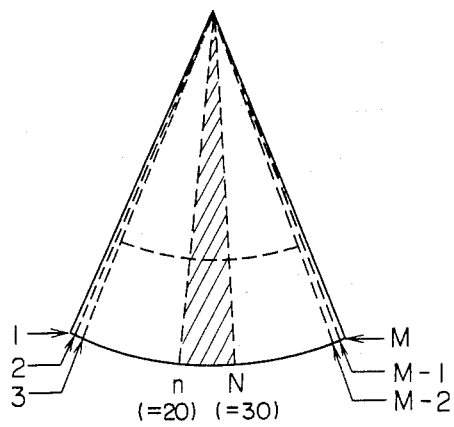
FIGS. 3 and 4 show different angles of scanning for the measurement of a Doppler blood flow image by the apparatus of the present invention.
Figure 4:
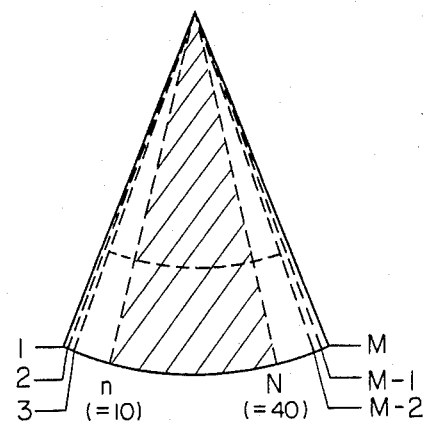

FIG. 2 shows schematically the principle of measurement of the speed of an internal moving part of a living body, for example, the speed of blood flow, by the ultrasonic diagnosis apparatus embodying the present invention. In order to measure the average speed of blood flowing through a blood vessel at a speed $v_0$ in a direction as shown by the arrow and to compute the speed dispersion and reflected wave intensity on the basis of the measured average speed, an ultrasonic pulse beam B is transmitted from the ultrasonic probe 1 to successively scan from a line address 1 to a line address M of a sectoral region shown in FIG. 2 such that an ultrasonic pulse is transmitted a plurality of times for each of individual scanning lines or a Doppler-mode scan is performed. When it is desired to change the angle of scanning for the measurement of a Doppler blood flow image, the desired scanning angle is designated by the Doppler scan angle designating circuit 24. In response to the designation of the scanning angle by the Doppler scan angle designating circuit 24, the transmitter control circuit 6 changes the address n of the Doppler scan starting line and the address N of the Doppler scan ending line and controls the transmitter circuit 4. Two forms of such a change in the scanning angle are shown in FIGS. 3 and 4. In each of FIGS. 3 and 4, the hatched portion represents the region for displaying a Doppler blood flow image, and the remaining portions represent the region for displaying a tomographic image. In FIG. 3, the address n of the scan starting line is 20, and the address N of the scan ending line is 30. When the scanning angle is changed as a result of designation by the Doppler scan angle designating circuit 24, the address n of the scan starting line and the address N of the scan ending line are changed to 10 and 40 respectively according to the designated scanning angle, as shown in FIG. 4.

Figure 5:
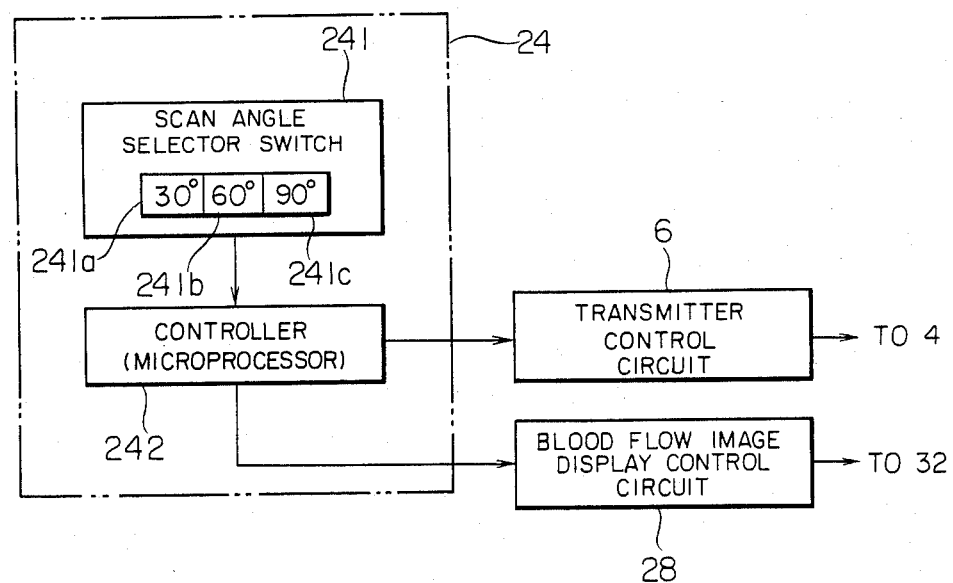
FIG. 5 shows the structure of one form of the Doppler scan angle designating circuit shown in FIG. 1.

FIG. 5 shows the structure of one form of the Doppler scan angle designating circuit 24. Referring to FIG. 5, the Doppler scan angle designating circuit 24 includes a scan angle selector switch 241 and a controller 242. The scan angle selector switch 241 selects one of a plurality of scanning angles arranged relative to the centerline of the scanning region shown in FIG. 2. In response to the application of the input signal from the selector switch 241, the controller 242 applies a command signal to the transmitter control circuit 6 so that the region between the line addresses n and N corresponding to the designated scanning angle can only be Doppler-scanned among the line address 1 to M of ultrasonic wave transmission. Also, the controller 242 applies a command signal to a blood flow image display control circuit 28 so that the blood flow image belonging to the region of the designated scanning angle can only be displayed on the display unit 29. This controller 242 can be easily embodied by a microprocessor. In FIG. 5, the selector switch 241 includes three push button keys 241a, 241b and 241c selecting three scanning angles of 30°, 60° and 90° respectively. However, it is apparent that the number of selectable scanning angles is in no way limited to three.

In operation, when it is desired to set the Dopper scanning angle at, for example, 60°, the key 241b of the selector switch 241 is depressed. In response to the depression of the key 241b, the scan starting and ending line addresses n and N corresponding to the scanning angle of 60° among the ultrasonic wave transmission line addresses 1 to M are computed by the microprocessor 242, and a command signal based on the result of computation is applied to the transmitter control circuit 6. In response to the application of the command signal, a command signal commanding ultrasonic pulse transmission for producing a usual ultrasonic tomographic image in the region between the scanning line addresses 1 and (n−1) is applied from the transmitter control circuit 6 to the transmitter circuit 4. In the region between the line addresses n and N, the transmitter control circuit 6 applies a command signal commanding ultrasonic pulse transmission for Doppler scanning that region, that is, a command signal commanding transmission of ultrasonic pulses a plurality of times for each of individual scanning lines. Also, in the region between the line addresses (N+1) and M, the transmitter control circuit 6 applies a command signal commanding ultrasonic pulse transmission for producing a usual ultrasonic tomographic image.

Each pulse reflected from the internal moving part of the living body is applied, after high-frequency amplification by the receiver amplifier 3, to the mixers 7, 8 and to the detector circuit 12. After being processed in the processing line including the mixers 7 and 8, the echo signal is stored in a display memory 32 after address designation by the blood flow image display control circuit 28. In this process, the microprocessor 242 controls the blood flow image display control circuit 28 so that the usual tomographic image signal may not be written in the display memory 32.

Figure 6:
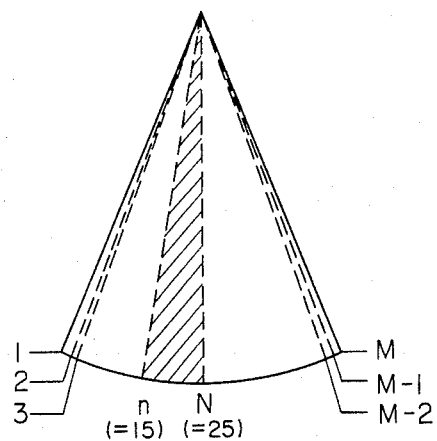
FIG. 6 shows a changed direction of scanning for the measurement of a Doppler blood flow image by the apparatus of the present invention.

When it is desired to change the direction of scanning for the measurement of the Doppler blood flow image, the desired direction is designated by the Doppler scan direction designating circuit 25. In response to the designation of the scanning direction by the Doppler scan direction designating circuit 25, the transmitter control circuit 6 changes the address n of the Doppler scan starting line and the address N of the Doppler scan ending line and controls the transmitter circuit 4. One form for such a change in the scanning direction is shown in FIG. 6. That is, FIG. 6 illustrates that the display region of the Doppler blood flow image show in FIG. 3 is changed as a result of the change in the scanning direction. In FIG. 6, the addresses n and N of the scan starting and ending lines are now changed to 15 and 25 respectively according to the change in the scanning direction.

Figure 7:
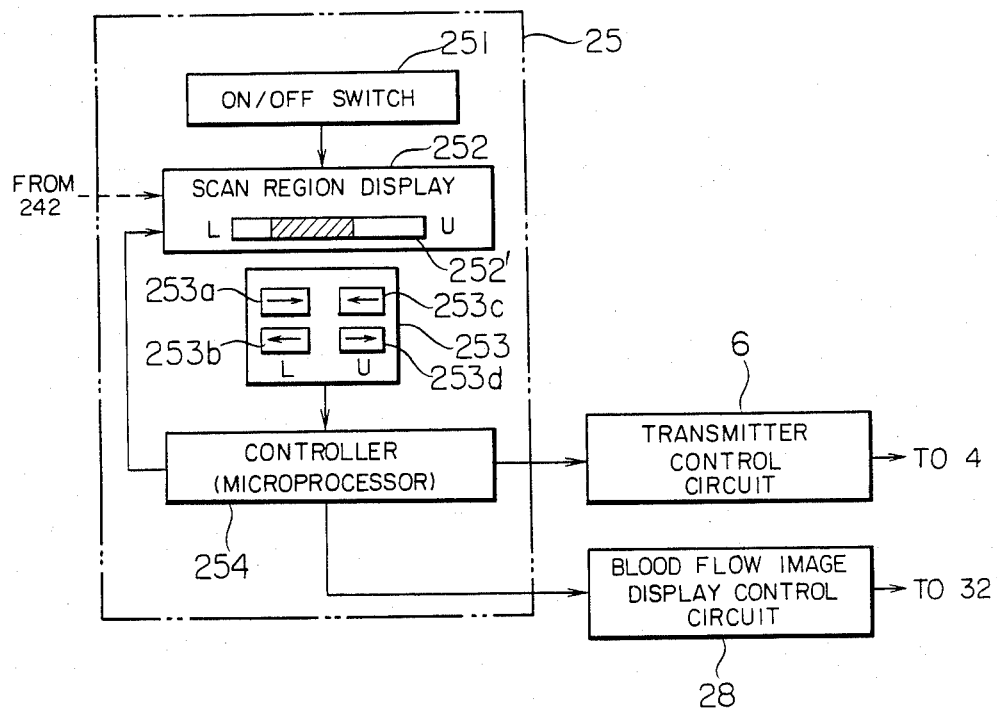
FIG. 7 shows the structure of one form of the Doppler scan direction designating circuit shown in FIG. 1.

FIG. 7 shows the structure of one form of the Doppler scan direction designating circuit 25. Referring to FIG. 7, the Doppler scan direction designating circuit 25 includes a scan region display 252 displaying a designated scanning region, an on-off switch 251 turning on-off the display 252, an address setting switch 253, and a controller 254. The scan region display 252 includes, for example, a bar-shaped liquid crystal display part 252'. The address setting switch 253 includes keys 253a, 253b for shifting the lowermost line address (the scan starting line address) in two directions and keys 253c 253d for shifting the uppermost line address (the scan ending line address) in two directions. One keying operation of each of these keys 253a to 253d corresponds to a shift of unit address. In response to the application of the input signal from the address setting switch 253, the controller 254 applies a command signal to the transmitter control circuit 6 so that the region between the uppermost line address and the lowermost line address corresponding to the designated scanning direction can only be Doppler-scanned among the line addresses 1 to M of ultrasonic pulse transmission. Also, the controller 254 applies a command signal to the blood flow image display control circuit 28 so that the blood flow image belonging to the Doppler scanning region can only be displayed on the display unit 29. This controller 254 is preferably a microprocessor similar to that providing the controller 242 shown in FIG. 5. A single microprocessor may act as both the controllers 254 and 242.

In operation, the entire region is first displayed on the display part 252' of the scan region display 252 in response to the depression of the switch 251. Then, when the desired keys of the address setting switch 253 are selectively repeatedly manipulated, the microprocessor 254 arithmetically processes the numbers of manipulation of the selected keys to compute the uppermost and lowermost line addresses. The microprocessor 254 feeds back the result of computation to the scan region display 252, so that the selected scanning region is displayed in almost real time on the scan region display 252, as shown by the hatched portion on the display part 252'. The operation of the apparatus thereafter under control of the microprocessor 254 is similar to that described already with reference to the Doppler scan angle designating circuit 24. The Doppler scan direction designating circuit 25 may be arranged for interlocking operation with the Doppler scan angle designating circuit 24. In such a case, it is preferable that uppermost and lowermost line address information corresponding to the selected scanning angle is supplied to the scan region display 252 from the controller 242 in the Doppler scan angle designating circuit 24 shown in FIG. 5 to display the corresponding scanning region on the display part 252', and the address setting switch 253 is then manipulated to shift the uppermost and lowermost line addresses of the scanning angle.

Figure 8:
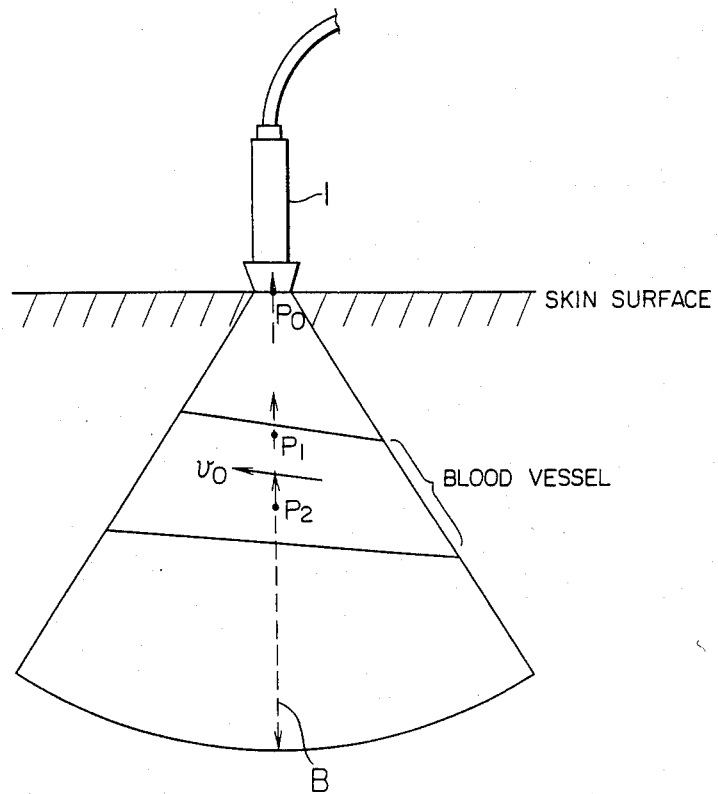
FIG. 8 illustrates schematically the manner of measurement of the distribution of the speed of an internal moving part of a living body, together with waves reflected from the living body.

A manner of variably setting the depth of scanning for the measurement of the Doppler blood flow image will now be described. FIG. 8 shows schematically the manner of measurement of the distribution of the speed of an internal moving part of a living body by transmission of the ultrasonic pulse beam. The ultrasonic pulse beam B transmitted from the ultrasonic probe 1 is reflected from various internal parts of the living body, as indicated by the symbols $P_0$, $P_1$ and $P_2$. No frequency shift occurs on the echo $P_0$ from an internal stationary part of the living body. However, in the case of the echoes $P_1$ and $P_2$ from an internal moving part such as blood flowing through a blood vessel, a frequency shift proportional to the speed of the internal moving part of the living body, that is, the speed $v_0$ of blood flow in the blood vessel occurs.

Figure 9A:
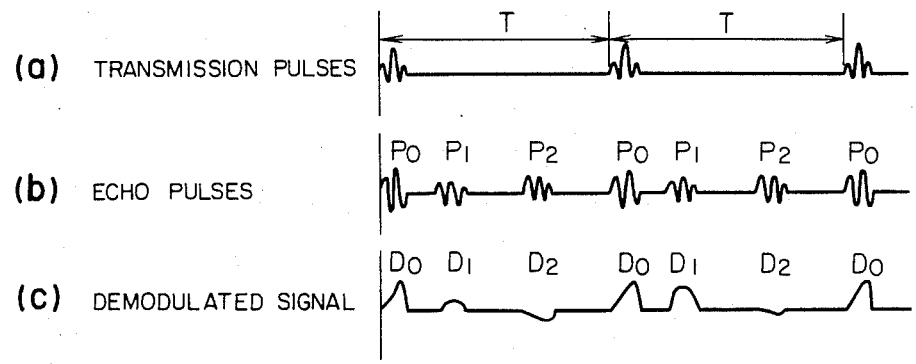
FIGS. 9A and 9B show waveforms of transmitted ultrasonic pulses, echo pulses and demodulated signals when a Doppler blood flow image is measured by a prior art ultrasonic diagnosis apparatus and the ultrasonic diagnosis apparatus of the present invention, respectively.
Figure 9B:
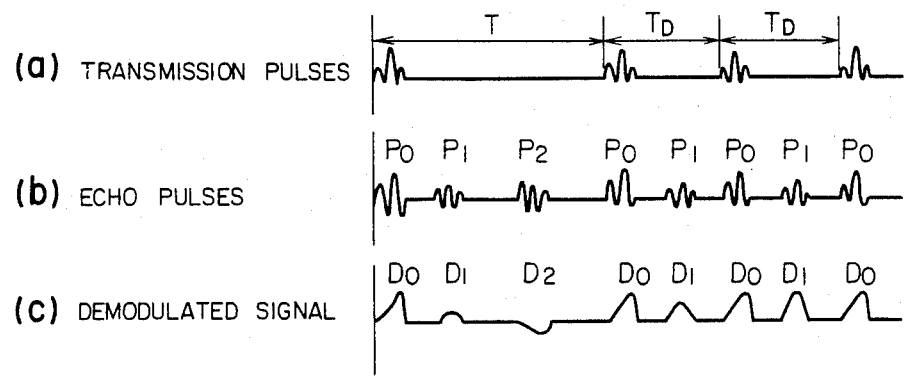

FIGS. 9A and 9B show signal waveforms observed during measurement of the speed of the internal moving part of the living body. In FIGS. 9A and 9B, the horizontal axis represents time, and the vertical axis represents the amplitude of signals. FIGS. 9A and 9B show in (a) the waveform of ultrasonic pulses transmitted toward and into the living body, in (b) the waveform of echo pulses from the living body, and in (c) the waveform of a signal obtained by demodulating the echo pulse signal by application of the reference signal having a frequency corresponding to the vibration frequency of the ultrasonic probe. In the case of a prior art, ultrasonic diagnosis apparatus, ultrasonic pulses transmitted for obtaining a Doppler blood flow image have a fixed interval T therebetween, and, therefore, the scanning depth is also constant, as seen in (a) of FIG. 9A. In contrast, in the case of the present invention, ultrasonic pulses are transmitted in a manner as shown in (a) of FIG. 9B, so that the depth of measurement of the Doppler signal is variable. That is, although the interval T between a first pulse and a second pulse transmitted to obtain a tomographic image is maintained constant, the interval $T_D$ between the second pulse and a third pulse and that between the third pulse and a fourth pulse, for example, are selected to be shorter than T. Thus, pulses $P_0$ and $P_1$ only are reflected from the internal moving part in response to the transmission of each of the second and third pulses. That is before arrival of an echo pulse $P_2$, the ultrasonic probe 1 acts to transmit the next ultrasonic pulse. By changing the pulse interval $T_D$ in the manner described above, the depth of scanning for the measurement of the Doppler blood flow image can be changed.

Such a method will be described with reference to FIG. 1. First, the depth of scanning for the measurement of a Doppler blood flow image is designated by the Doppler scan depth designating circuit 26 shown in FIG. 1. Then, the transmitter control circuit 6 controls the transmitter circuit 4 so that the depth of scanning with the ultrasonic pulse beam becomes equal to the value designated by the Doppler scan depth designating circuit 26.

Figure 10:
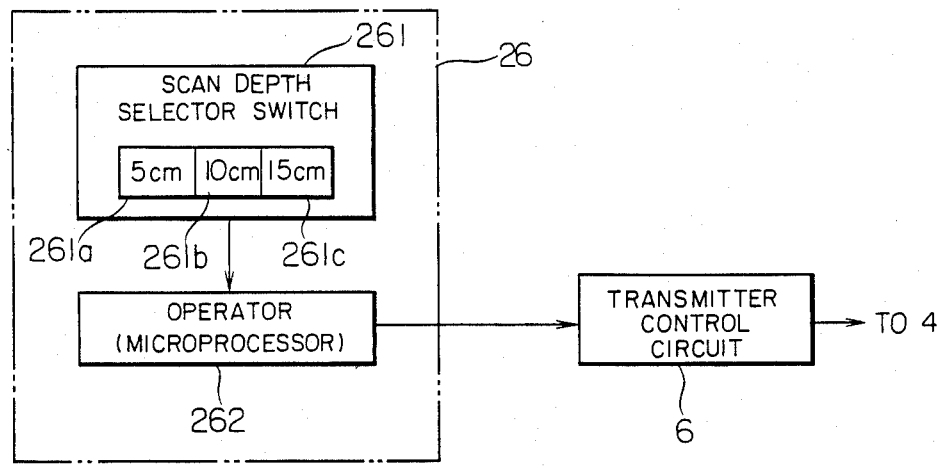
FIG. 10 shows the structure of one form of the Doppler scan depth designating circuit shown in FIG. 1.

FIG. 10 shows the structure of one form of the Doppler scan depth designating circuit 26. Referring to FIG. 10, the Doppler scan depth designating circuit 26 includes a scan depth selector switch 261 selecting one of a plurality of depths scanned with the ultrasonic pulse beam, and an operator 262 which, in response to the input signal applied from the selector switch 261, computes the transmission time interval, that is, the penetration distance of the transmitted ultrasonic pulse beam and applies a command signal to the transmitter control circuit 6. This operator 262 is preferably in the form of a microprocessor as in the case of the controllers 242 and 254 shown in FIGS. 5 and 7 respectively. In the form shown in FIG. 10, the selector switch 261 includes three push button keys 261a, 261b and 261c for selecting three scanning depths of 5 cm, 10 cm and 15 cm respectively. It is apparent that the number of selectable scanning depths is in no way limited to three.

In operation, in response to the depression of a selected one of the keys 261a to 261c of the selector switch 261, the microprocessor 262 computes the time interval $T_D$ of ultrasonic pulse transmission corresponding to the selected scanning depth (distance) and applies the resultant command signal to the transmitter control circuit 6 which controls the transmitter circuit 4 generating the ultrasonic pulse transmission command signal. The transmitter circuit 4 controlled by the transmitter control circuit 6 applies the transmission command signal to the ultrasonic probe 1 so as to transmit ultrasonic pulses according to the time sequence shown in (a) of FIG. 9B.

The manner of displaying the Dopper blood flow image and tomographic image will now be described. Tomographic image data written in the image memory 15 in the manner described above are read out from the image memory 15 under control of the address generator 20 and are converted by the D/A converter 16 into an analog signal voltage (a luminance modulation signal). This analog signal is applied through a change-over circuit 36, which is controlled by a display control circuit 35 to change over between the Doppler blood flow image signal and the tomographic image signal, to the display unit 29 to be displayed on the display unit 29 as the tomographic image in synchronism with a synchronizing signal applied from a TV synchronizing circuit 34. On the other hand, Doppler blood flow image data are stored in a memory 32 under control of the blood flow image display control circuit 28 which controls the data writing address of the memory 32. The Doppler blood flow image data stored in the memory 32 are read out from the memory 32 under control of an address generator 33 and are converted by a D/A converter 31 into an analog signal. This analog signal is applied though a Doppler blood flow image/tomographic image change-over circuit 30 controlled by the display control circuit 35 to the display unit 29 to be displayed on the display unit 29 as the Doppler blood flow image in synchronism with the synchronizing signal applied from the TV synchronizing circuit 34.

The change-over circuits 30 and 36 may be controlled by the display control circuit 35 so that the tomographic image and the Doppler blood flow image are displayed in superposed relation.

Figure 11:
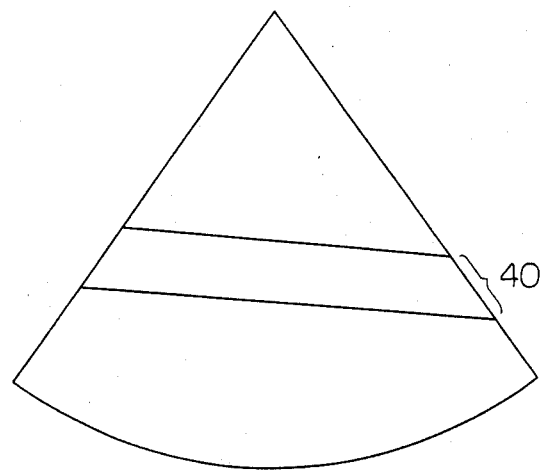
FIG. 11 illustrates the region of scanning and display for the measurement of a tomographic image and a Doppler blood flow image in the case of the prior art ultrasonic diagnosis apparatus.
Figure 12:
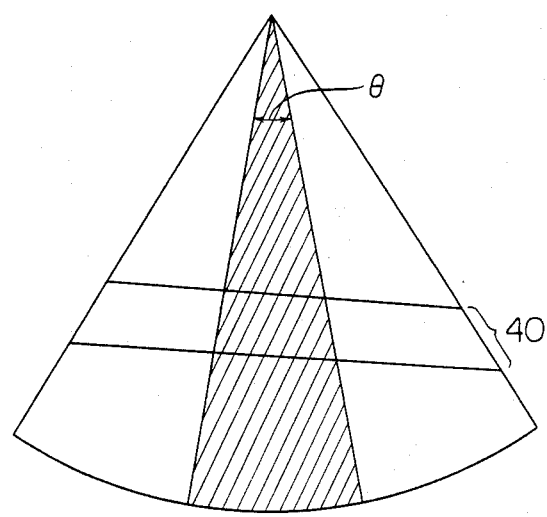
FIGS. 12 to 14 illustrate the regions of scanning and display for the measurement of a tomographic image and a Doppler blood flow image in the case of the ultrasonic diagnosis apparatus according to the present invention.
Figure 13:
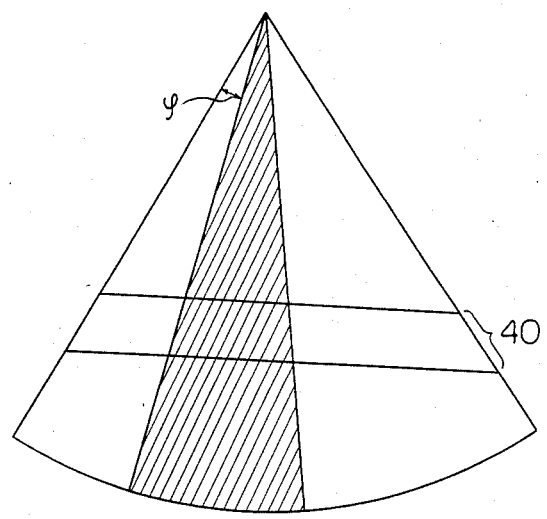
Figure 14:
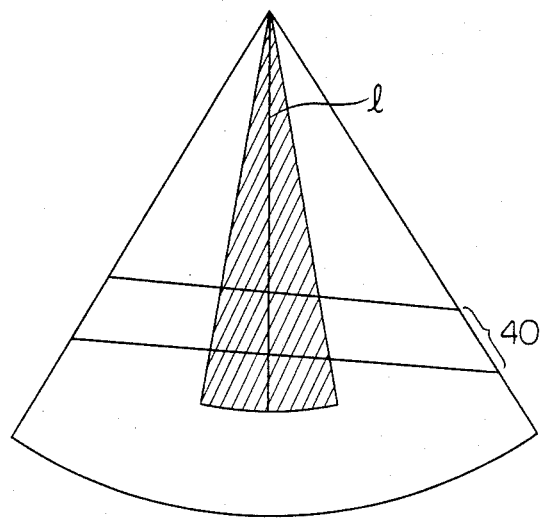

FIG. 11 illustrates the region of scanning and display for displaying a tomographic image and a Doppler blood flow image of blood flowing through a blood vessel 40, in the case of a prior art ultrasonic diagnosis apparatus. In contrast, FIG. 12 illustrates the case of the present invention according to which the scanning angle can be selected as desired. In FIG. 12, the hatched portion represents the region for displaying a Doppler blood flow image, and the remaining portions represents the region for displaying a tomographic image. Also, in FIG. 12, the symbol $\theta$ represents the scanning angle for measurement of the Doppler blood flow image. Also, according to the present invention in which the scanning direction can be selected as desired, the direction of the displayed Doppler blood flow image can be changed as desired, as illustrated in FIG. 13. That is, the angle $\psi$ defined between the Doppler blood flow image and the tomographic image can be changed as desired. Further, according to the present invention in which the scanning depth can be selected as desired, the depth l of the displayed Doppler blood flow image can be changed as desired, as illustrated in FIG. 14.

The embodiment of the apparatus described in the foregoing is provided with all of the designating circuits 24, 25 and 26 designating the angle, direction and depth of scanning respectively. However, it is apparent that various combinations of these designating circuits may be selected depending on the performance vs. cost ratio and intended services.

In the present invention, an ultrasonic probe of sector type has been referred to, by way of example. It is apparent, however, that the effect similar to that described above can be exhibited by employment of an ultrasonic probe of linear type or convex type.

Further, the present invention has referred to employment of an ultrasonic wave transmission and reception scheme usually practiced in this field of art. However, a method, in which an ultrasonic pulse beam transmitted in one direction is received as echoes from multiple directions, as disclosed in Japanese Patent Applications Nos. 60-31148 and 60-31150 (1985), may be employed, so as to increase the frame rate thereby further shortening the image completion time.

The present invention provides various advantages as follows:

(1) The direction and/or the depth of scanning with an ultrasonic pulse beam can be selected as desired, so that the image completion time of a Doppler blood flow image can be shortened, and undesirable flickering of the Doppler blood flow image can be minimized.

(2) By adequately selecting the scanning angle and/or the scanning depth, scanning and display of portions of the Doppler blood flow image considered to be unnecessary for diagnosis can be omitted, so that the displayed image can be more easily diagnosed.

(3) Since the scanning direction can be selected as desired, the Doppler blood flow image of a portion to be examined in detail can be easily obtained, thereby improving the operability and facilitating the diagnosis.

(4) By the combination of the individual methods of setting the scanning angle, scanning direction and scanning depth, the combination of the advantages described in (1), (2) and (3) can be attained.

We claim:

1. An ultrasonic diagnosis apparatus comprising:
a single ultrasonic wave transmitting and receiving means for transmitting an ultrasonic pulse beam into a living body at a predetermined recurrence frequency to scan a scanning region and for receiving reflected waves therefrom;
B-mode scanning means for causing said single ultrasonic wave transmitting and receiving means to perform a B-mode scan, such that an ultrasonic pulse beam is transmitted in a plurality of directions and received as reflected-echo signals from said plurality of directions, for producing an ultrasonic image;
Doppler-mode scanning means for causing said single ultrasonic wave transmitting and receiving means to perform a Doppler-mode scan, such that an ultrasonic pulse beam is transmitted into said living body in a plurality of directions and received as reflected-echo signals from said plurality of directions, for producing an ultrasonic image;
B-mode image producing means for performing first image-processing with respect to said reflected-echo signals received through said B-mode scan which correspond to a predetermined cross-sectional are in said living body and for storing resultant B-mode image data after said first image-processing;
Doppler-mode image producing means for determining a Doppler frequency shift between said reflected-echo signals received through said Doppler-mode scan, for performing second image-processing with respect to said reflected-echo signals with shifted frequencies for producing a Doppler image of a moving part in said living body, and for storing resultant Doppler-mode image data after said second image-processing;
display means for reading the stored B-mode image data from said B-mode image producing means and the stored Doppler-mode image data from said Doppler-mode image producing means and for displaying said B-mode image data and said Doppler-mode image data as a two-dimensional image; and
Doppler scanning area designating means for supplying to said Doppler-mode scanning means a command which causes said Doppler-mode scanning means to variably designate said Doppler scanning area.

2. An ultrasonic diagnosis apparatus according to claim 1, wherein said Doppler scanning area designating means includes scanning angle designating means capable of designating a Doppler scanning angle symmetrically with respect to a center axis line of said scanning region in said living body.

3. An ultrasonic diagnosis apparatus according to claim 2, wherein said scanning angle designating means includes means for selecting one of a plurality of different predetermined angles as said Doppler scanning angle and means for controlling said Doppler scanning means and said display means using an output signal from said selecting means.

4. An ultrasonic diagnosis apparatus according to claim 1, wherein said Doppler scanning area designating means includes scanning direction designating means capable of designating said Doppler scanning area asymmetrically with respect to a center axis line of said scanning region in said living body.

5. An ultrasonic diagnosis apparatus according to claim 4, wherein said scanning direction designating means includes scanning direction indicating means for designating ultrasonic pulse beam directions on opposite extreme sides of said Doppler scanning area and control means for processing an output signal from said scanning direction indicating means to produce an output signal which causes said Doppler scanning means and said display means to perform said Doppler-mode scan and to display said Doppler-mode image corresponding to said designated scanning area.

6. An ultrasonic diagnosis apparatus according to claim 5, wherein said scanning direction designating means includes means for converting an output signal from said control means into a visual signal to display a position of said Doppler scanning area in said scanning region.

7. An ultrasonic diagnosis apparatus according to claim 1, wherein said Doppler scanning area designating means includes scanning depth designating means capable of variably designating a scanning depth for said Doppler-mode scan which is shallower than a scanning depth of said B-mode scan by said B-mode scanning means.

8. An ultrasonic diagnosis apparatus according to claim 7, wherein said scanning depth designating means includes means for selecting one of a plurality of depths as said scanning depth in said Doppler-mode scan and means for determining, based on an output signal from said selecting means, a transmission interval for said ultrasonic pulse beams transmitted in said Doppler-mode scan from said ultrasonic wave transmitting and receiving means to control said Doppler-mode scanning means in accordance with the determined transmission interval.

9. An ultrasonic diagnosis apparatus according to claim 1, wherein said Doppler-scanning area designating means includes at least two of scanning angle designating means capable of designating a Doppler scanning angle symmetrically with respect to a center axis line of said scanning region of said single ultrasonic wave transmitting and receiving means, scanning direction designating means capable of designating said Doppler scanning area asymmetrically with respect to the center axis line of said scanning region of said single ultrasonic wave transmitting and receiving means, and scanning depth designating means capable of variably designating a scanning depth which is shallower than a scanning depth of said B-mode scan by said B-mode scanning means.

10. An ultrasonic diagnosis apparatus according to claim 1, wherein said display means includes a visual CRT on which said B-mode image and said Doppler-mode image are displayed.

11. An ultrasonic diagnosis apparatus comprising:
a single ultrasonic wave transmitting and receiving means including a single array of oscillators for transmitting an ultrasonic pulse beam into a living body at a predetermined recurrence frequency to cover a scanning region and for receiving reflected waves therefrom;
B-mode scanning means for causing said single ultrasonic wave transmitting and receiving means to perform a B-mode scan for producing an ultrasonic image, such that an ultrasonic pulse beam is transmitted in a plurality of directions of a certain cross section in said living body, each of said plurality of directions defining a scanning line and each ultrasonic pulse beam being received as reflected-echo signals along each of said scanning lines;
Doppler-mode scanning means for causing said single ultrasonic wave transmitting and receiving means to perform a Doppler-mode scan for producing an ultrasonic image, such that an ultrasonic pulse beam is transmitted in a plurality of directions for a certain cross section in said living body a plurality of times for each of said scanning lines, each said ultrasonic pulse beam being received as reflected-echo signals;
B-mode image producing means for performing first image-processing with respect to said reflected-echo signals received through said B-mode scan which correspond to a predetermined cross-sectional area in said living body and for storing resultant B-mode image data after said first image-processing;
Doppler-mode image producing means for determining a Doppler frequency shift between said reflected-echo signals received through said Doppler-mode scan, for performing second image-processing with respect to said reflected-echo signals with shifted frequencies for producing a Doppler image of a moving part in said living body, and for storing resultant Doppler-mode image data after said second image-processing;
display means for reading the stored B-mode image data from said B-mode image producing means and the stored Doppler-mode image data from said Doppler-mode image producing means and for displaying said B-mode image data and said Doppler-mode image data as a two-dimensional image corresponding to a position thereof in said living body;
connecting means capable of one of alternately and simultaneously connecting said B-mode image producing means and said Doppler-mode image producing means to said display means; and
Doppler scanning area designating means for supplying to said Doppler-mode scanning means a command which causes said Doppler-mode scanning means to variably designate a Doppler scanning area.

12. An ultrasonic diagnosis apparatus according to claim 11, wherein said single ultrasonic wave transmitting and receiving means includes one of an ultrasonic probe of sector scan type, an ultrasonic probe of linear type and an ultrasonic probe of convex scan type.

13. An ultrasonic diagnosis apparatus according to claim 11, wherein said display means includes a visual CRT on which said B-mode image and said Doppler-mode image are displayed.

* * * * *